United States Patent
Cox et al.

(10) Patent No.: US 6,569,193 B1
(45) Date of Patent: May 27, 2003

(54) TAPERED SELF-EXPANDING STENT

(75) Inventors: Daniel L. Cox, Palo Alto, CA (US); Kent C. B. Stalker, San Diego, CA (US); Joe Ventura, II, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/359,550

(22) Filed: Jul. 22, 1999

(51) Int. Cl.[7] ................................................. A61F 2/06
(52) U.S. Cl. ..................................... 623/1.15; 623/1.31
(58) Field of Search .............................. 623/1.15, 1.18, 623/1.3, 1.31, 1.34

(56) References Cited

U.S. PATENT DOCUMENTS

| | | | |
|---|---|---|---|
| 4,441,215 A | 4/1984 | Kaster | |
| 5,180,392 A | 1/1993 | Skeie et al. | |
| 5,222,964 A | 6/1993 | Cooper | |
| 5,569,295 A | * 10/1996 | Lam | 606/195 X |
| 5,591,197 A | * 1/1997 | Orth et al. | 623/1.16 |
| 5,725,572 A | * 3/1998 | Lam et al. | 606/191 X |
| 5,827,321 A | 10/1998 | Roubin et al. | |
| 5,843,117 A | 12/1998 | Alt et al. | |
| 5,855,600 A | * 1/1999 | Alt | 623/1.15 |
| 5,911,732 A | * 6/1999 | Hojeibane | 623/1.11 |
| 5,911,754 A | * 6/1999 | Kanesaka et al. | 623/1.15 |
| 5,925,061 A | * 7/1999 | Ogi et al. | 623/1.2 |
| 5,938,697 A | * 8/1999 | Killion et al. | 623/1.15 |

FOREIGN PATENT DOCUMENTS

WO    WO 98/53759    3/1998

\* cited by examiner

*Primary Examiner*—Paul B. Prebilic
*Assistant Examiner*—Brian E. Pellegrino
(74) *Attorney, Agent, or Firm*—Fulwider Patton Lee & Utecht, LLP

(57) ABSTRACT

A self-expanding, tapered profile stent for implantation in a body lumen, such as an artery, is disclosed. The stent is constructed of a plurality of radially expandable cylindrical elements generally aligned on a common longitudinal stent axis and interconnected by one or more interconnecting members placed so that the stent is flexible in the longitudinal direction. The lengths of the cylindrical elements increase from one end of the stent to the opposite end by increasing the lengths of the struts and the lengths of the interconnecting members. Each cylindrical element is formed from repeating patterns of upright V's and inverted V's connected by straight strut arms with shoulders to create an overall serpentine wave pattern around the circumference. A step, continuous, parabolic, or curved taper in the stent can be imparted by using an expansion mandrel and applying deforming forces to the stent. The stent is made from pseudoelastic and shape memory alloys.

2 Claims, 4 Drawing Sheets

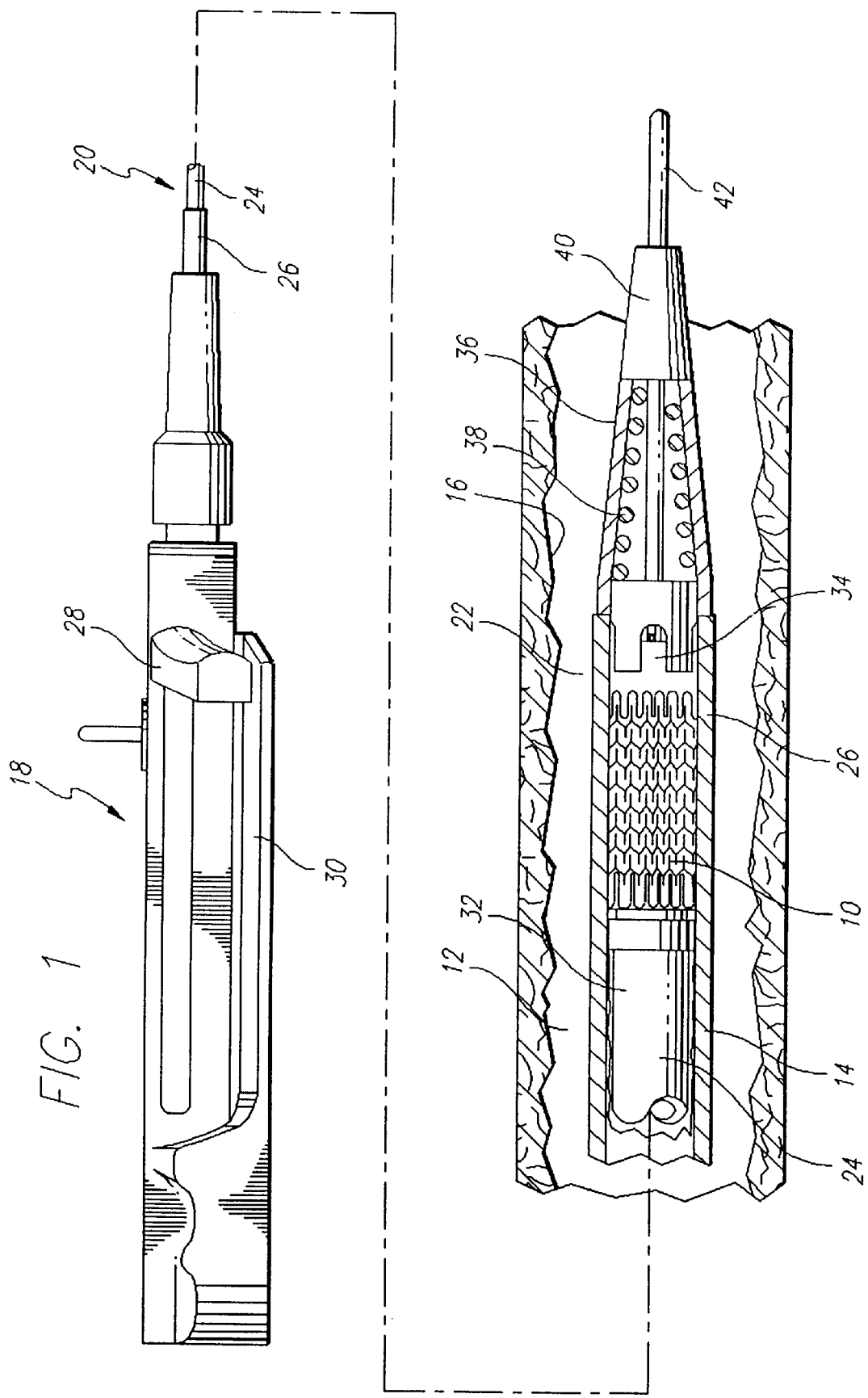

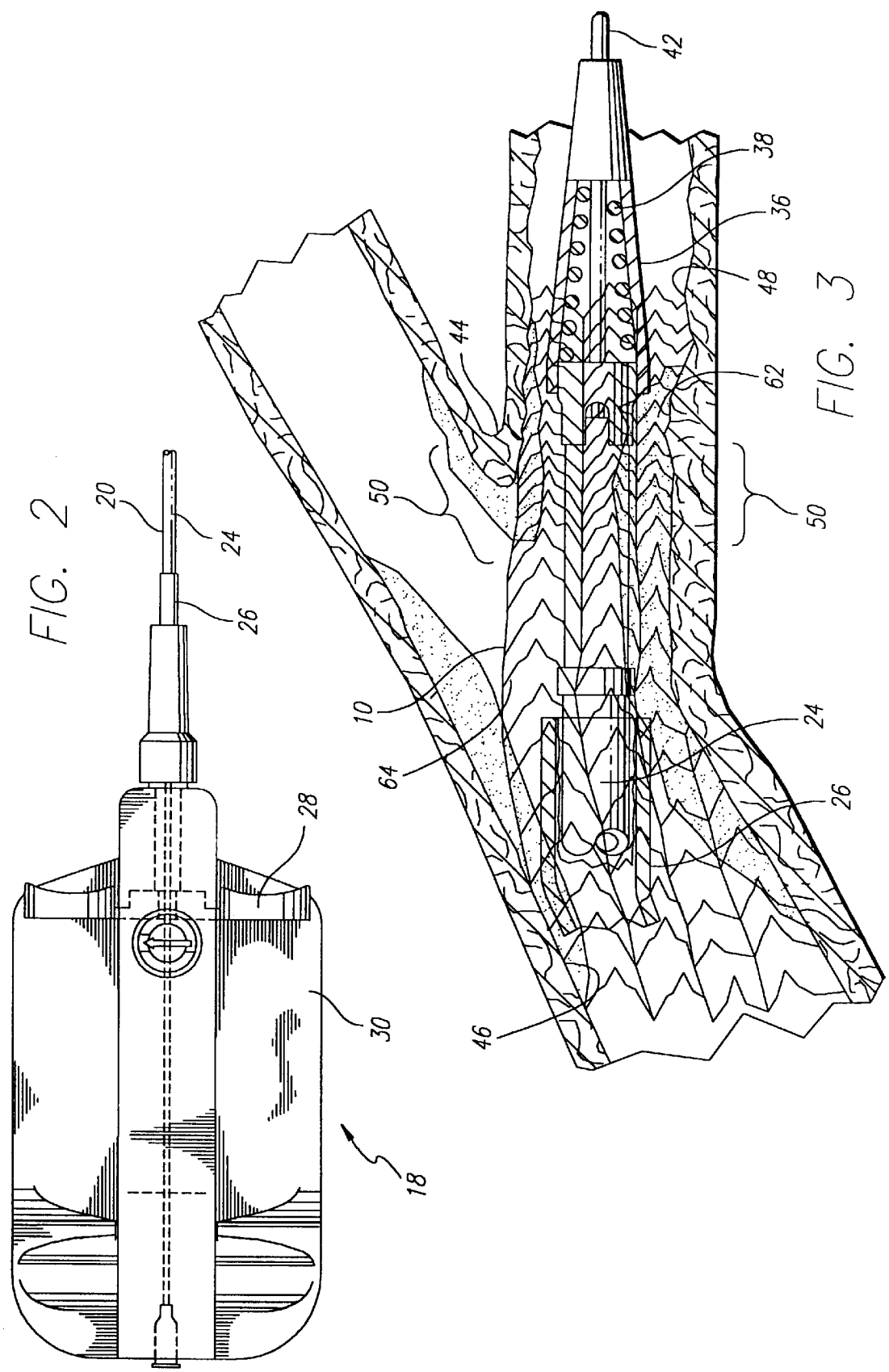

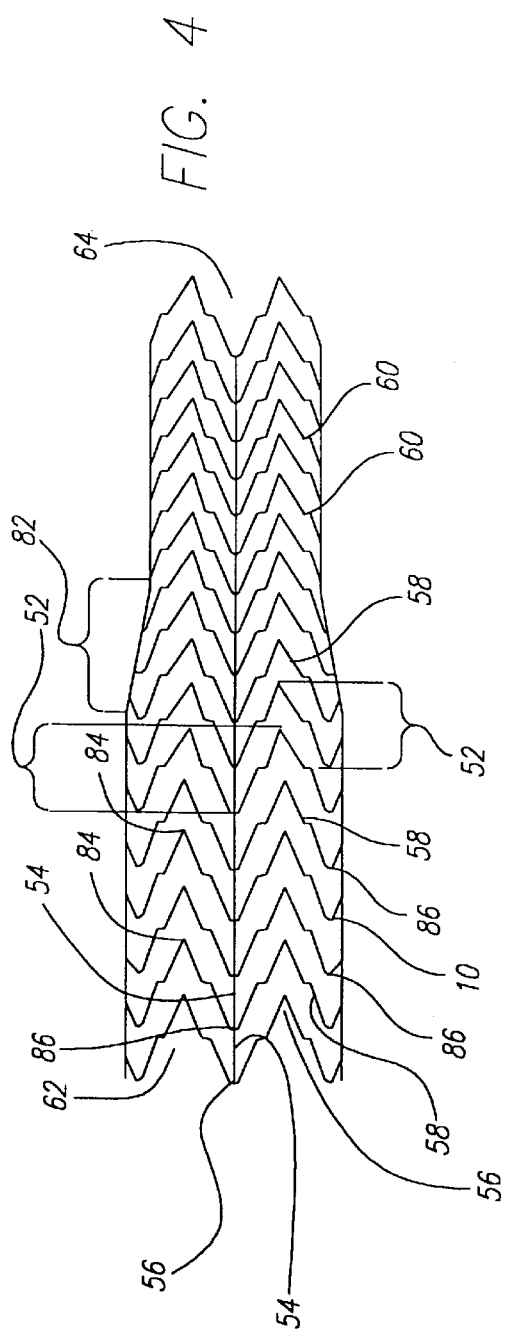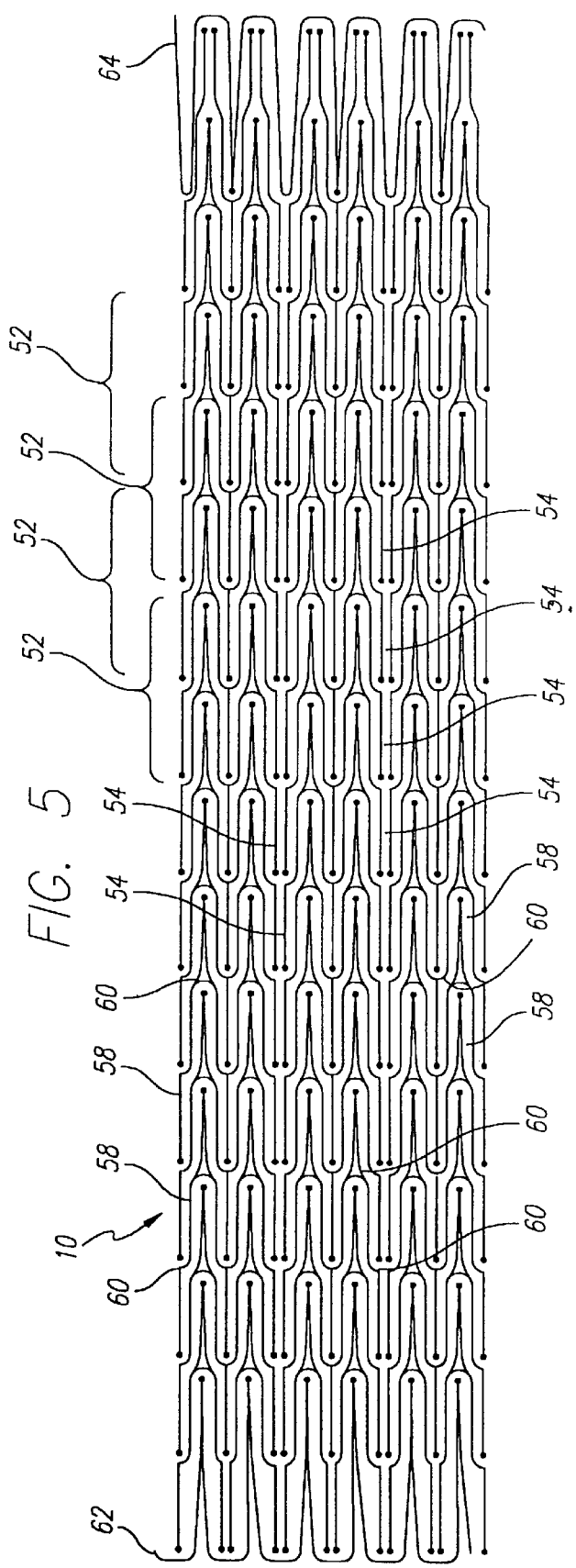

TAPERED SELF-EXPANDING STENT

BACKGROUND OF THE INVENTION

The present invention relates to expandable endoprosthesis devices, generally known as stents, which are designed for implantation in a patient's body lumen, such as blood vessels, to maintain the patency thereof. These devices are particularly useful in the treatment and repair of blood vessels after a stenosis has been compressed by percutaneous transluminal coronary angioplasty (PTCA), percutaneous transluminal angioplasty (PTA), or removed by atherectomy or other means.

Stents are typically implanted within a vessel in a contracted state and expanded when in place in the vessel in order to maintain patency of the vessel to allow fluid flow through the vessel. Ideally, implantation of such stents is accomplished by mounting the stent on the balloon portion of a catheter, positioning the stent in a body lumen at the stenosis, and expanding the stent to an expanded state by inflation of the balloon within the stent. The stent can then be left in place by deflating the balloon and removing the catheter.

A bifurcated stenosis typically can occur in the carotid or coronary arteries at the carina between adjoining arterial branches and around the ostia of the adjoining arterial branches. Employment of a stent for repair of vessels that are diseased at a bifurcation requires that the stent must, without compromising blood flow, overlay the entire circumference of the ostium to a diseased portion and extend to a point within and beyond the diseased portion. Particularly at a bifurcation, lesions may form along the side walls of the blood vessel and at the carina of the bifurcation, not only contributing to stenosis of a main branch and side branch of the bifurcation, but also interfering with the normal rheology of flow at the bifurcation to create eddy currents that can contribute to formation of thrombosis.

A conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying the circumference of the ostium to the diseased portion. Such placement of the conventional stent results in a bifurcation that is not completely repaired. Also, where the stent does not overlay the entire circumference of the ostium to the diseased portion, the stent fails to completely repair the bifurcated vessel.

In a conventional method for treating bifurcated vessels, the side-branch vessel is first stented so that the stent protrudes into the main vessel. A dilatation is then performed in the main vessel to open and stretch the stent struts extending across the lumen from the side-branch vessel. Thereafter, the main-vessel stent is implanted so that its proximal end overlaps with the side-branch vessel. However, the structure of the deployed stent must be recrossed with a wire by trial and error.

In another prior art procedure, known as "kissing" stents, a stent is implanted in the main vessel with a side-branch stent partially extending into the main vessel creating a double-barreled lumen of the two stents in the main vessel proximal to the bifurcation. Another prior art approach includes a so-called "trouser legs and seat" approach, which includes implanting three stents, one stent in the side-branch vessel, a second stent in a distal portion of the main vessel, and a third stent, or a proximal stent, in the main vessel just proximal to the bifurcation.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the distal segment, but not extending into the ostium of the distal side-branch, may be difficult or impossible.

It is important for stents to be sized correctly for the vessel into which they are implanted. In some situations, like the carotid artery, it is desirable to place a single stent from the common carotid artery to the internal carotid artery. The diameter is about 2 to 3 mm smaller in the internal carotid artery, so it is difficult to size a stent appropriately for both vessels. A stent that is designed for a large diameter vessel is not optimal for a small diameter vessel, and vice versa.

To address the deployment problems at a bifurcation and to address the stent sizing problems, the present invention is directed to a tapered stent. With such a tapered stent, the diameter of the stent varies along the length of the stent.

Some tapered stent designs are known in the art. For example, PCT Publication No. WO98/53759, entitled "Carotid Stent," by Jay S. Yadav discloses a stent for cardiovascular application wherein a substantially cylindrical tubular member tapers from its proximal end to its distal end. This type of tapered stent is intended for stenting the common carotid bifurcation or the proximal internal carotid artery.

PCT Publication No. WO98/34668, entitled "Non-Foreshortening Intraluminal Prosthesis" by Gary S. Roubin et al. discloses an intraluminal prosthesis provided with a plurality of annular elements. The stent may be provided with varying flexibility along its length and/or circumference, and may include segments that have different diameters. The differing diameters may be accomplished by providing the stent in a tapered or a stepped configuration.

Other tapered stents include U.S. Pat. No. 5,222,964 to Cooper, disclosing a tapered stent made of resilient material for interconnecting portions of a Fallopian tube after a resection procedure. U.S. Pat. No. 5,180,392 to Skeie et al. discloses a prosthesis for use in joining hollow organ parts or systems wherein the prosthesis may have tapered outer ends. U.S. Pat. No. 4,441,215 to Kaster discloses a vascular graft of a synthetic material including a tubular member having a braided inner layer and a compliant outer covering layer. This synthetic vascular graft can have an increasing or decreasing taper.

Another tapered stent is known as the "Flamingo Wallstent." The Flamingo Wallstent is intended for esophageal malignant strictures. It is partially covered at the ends to protect against tissue injury, and inside to prevent food impaction and tumor growth. A major drawback for the Flamingo Wallstent design is its inability to be accurately placed due to unpredictable foreshortening after deployment.

There is, however, still a need for an improved tapered stent for deployment in, for example, the common carotid bifurcation or the proximal internal carotid artery. These areas are the most common sites for cerebrovascular atherosclerotic disease.

SUMMARY OF THE INVENTION

To address the aforementioned problems, the present invention is directed to a stent having a taper along its length and having varying radial strength as a function of the diameter of the stent and spacing between the struts. In a preferred embodiment, the present invention is directed to a longitudinally flexible stent for implanting in a body lumen and expandable from a contracted condition to an expanded condition, comprising a plurality of adjacent cylindrical elements, each cylindrical element having a circumference extending around a longitudinal axis and being substantially independently expandable in the radial direction, wherein the plurality of adjacent cylindrical elements are arranged in alignment along the longitudinal stent axis, and wherein a plurality of cylindrical elements include sequentially increasing diameters to create a tapered profile, with each cylindrical element formed from struts arranged in a serpentine wave pattern; and a plurality of interconnecting members extending between the adjacent cylindrical elements and connecting the adjacent cylindrical elements to one another; wherein the struts and interconnecting members at the tapered profile increase in length along the longitudinal stent axis.

Such a tapered stent with smaller diameters as well as larger diameters has several benefits. A stent having a smaller diameter can have greater radial strength, better coverage of the vessel wall, and less foreshortening than is achievable with a stent having larger diameters. Obtaining these optimized features is especially important for the carotid application in which the internal carotid artery has the most significant disease, but the common carotid artery diameter dictates many of the design requirements of the stent.

As mentioned earlier, carotid stent procedures frequently involve the treatment of a diseased artery where plaque extends across the bifurcation between the common and internal carotid arteries. Selection of an appropriate stent diameter becomes precarious because the internal carotid artery tends to be smaller than the parent common carotid artery. The stent selected must be large enough to treat the common carotid artery, but using a stent sized to the common carotid artery can require implantation of a stent much larger than the nominal diameter of the internal carotid artery. This stent diameter mismatch and concomitant oversizing could lead to vessel injury and poor clinical results.

In the present invention, each end of the stent has preferably been designed specifically for the appropriate diameter range. That is, when deployed, the smaller diameter end of the stent supports the diseased portion of the internal carotid artery while the larger diameter end of the tapered stent supports the large diameter of the common carotid artery.

The present invention can be made from a shape-memory metallic alloy such as Nitinol or superelastic Nitinol to create a self-expanding stent. Alternatively, the present invention stent can be balloon expanded. With a balloon expandable stent, the shape of the balloon can be used to control the final shape of the stent. For example, a balloon with more than one diameter can be used to expand a stent having two final diameters. Separate balloons can also be used to post dilate the stent with a step in its diameter.

The present invention tapered stent presents a logical solution for carotid stenting across the bifurcation. The varying stent diameter accomplishes at least two goals: it allows adequate treatment of a lesion in both the common and internal carotid while maintaining a suitable stent-to-artery ratio for each vessel.

Other features and advantages of the present invention will become more apparent from the following detailed description of the invention, when taken in conjunction with the accompanying exemplary drawings.

BRIEF DESCRIPTION OF THE DRAWINGS

FIG. 1 is a side elevational view depicting the present invention stent and a deployment system as the stent is carried through a vessel.

FIG. 2 is a top plan view of a handle of the deployment system.

FIG. 3 is a cross-sectional view of the present invention tapered stent after deployment at the bifurcation between the common and internal carotid arteries.

FIG. 4 is a perspective view of a preferred embodiment of the present invention tapered stent in its expanded mode.

FIG. 5 is a plan view of a flattened strut pattern of the present invention tapered stent in its unexpanded mode.

DETAILED DESCRIPTION OF THE PREFERRED EMBODIMENTS

Figure 6:
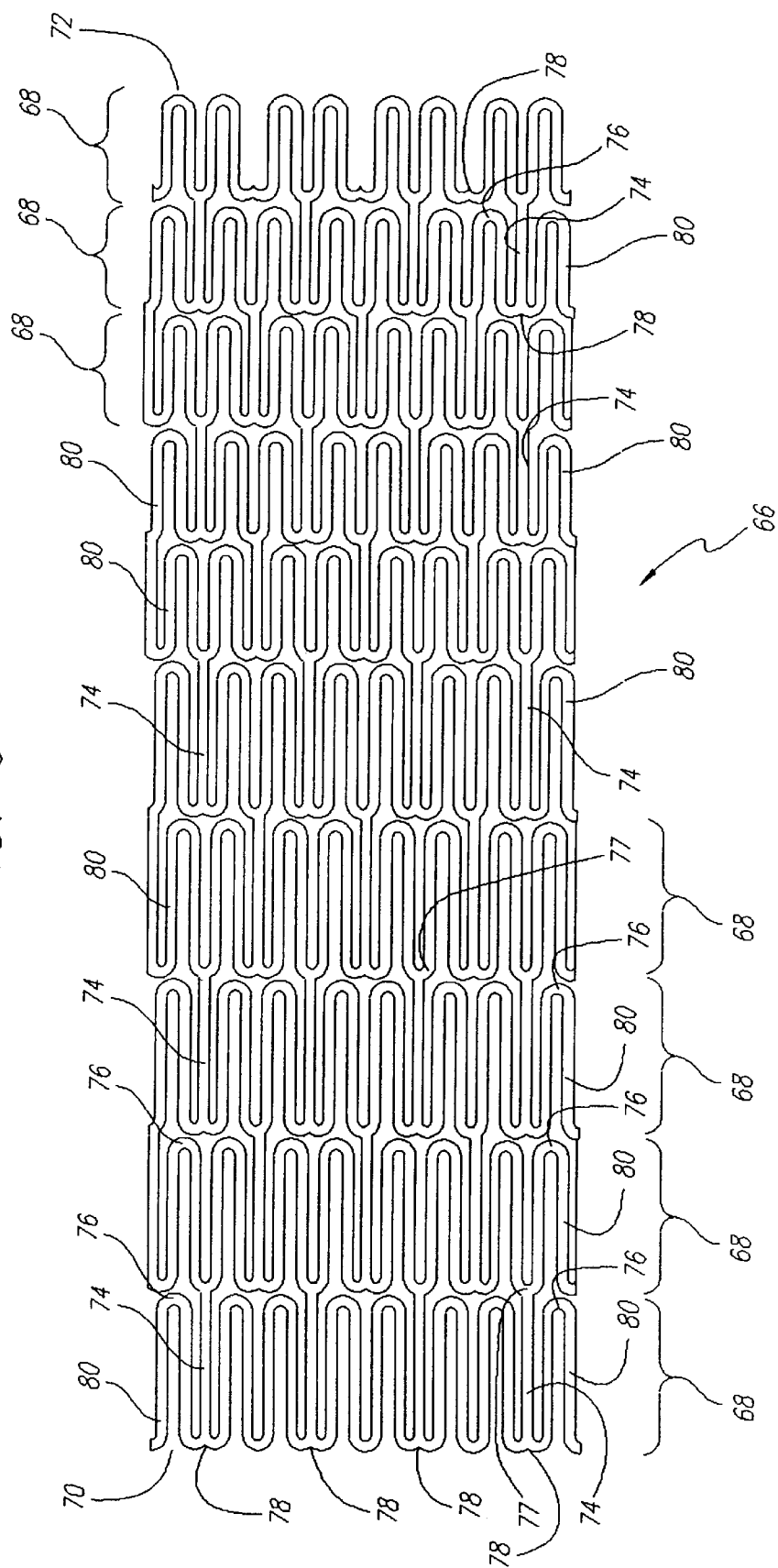
FIG. 6 is a plan view of a flattened strut pattern of an alternative embodiment tapered stent in its unexpanded mode.

The present invention is directed to a tapered stent with a strut pattern that changes the spacing between struts to achieve various design objectives. While the present invention is described in detail as applied to the carotid artery of a patient, those skilled in the art will appreciate that the present invention can also be used in other body lumens as well.

FIG. 1 is a side elevational view and partial sectional view of self-expanding stent 10 of the present invention as carried inside stent delivery system 12. Stent delivery system 12 includes elongated catheter body 14 for delivering and deploying stent 10 which is shown in the compressed or unexpanded state. As seen in FIG. 1, elongated catheter body 14 is positioned within artery 16 or similar type vessel.

Stent delivery system 12 further includes housing assembly 18 attached to proximal end 20 of delivery catheter 14. Housing assembly 18 is used to manually deploy compressed stent 10 mounted at distal end 22 of delivery catheter 14. Delivery catheter 14 further includes inner tubular member 24 that extends within outer tubular member 26 in a coaxial arrangement.

Outer tubular member 26 has a proximal end attached to pull-back handle 28 that is designed to move along the longitudinal axis of delivery catheter 14 while supported by base 30 of housing assembly 18. When pull-back handle 28 is translated in the proximal direction, outer tubular member 26 is likewise translated in the proximal direction exposing compressed stent 10. Because base 30 of housing assembly 18 remains stationary, inner tubular member 24 also remains stationary during the stent deployment.

Applying tensile force to the shaft of outer tubular member 26 during stent deployment creates an equal and opposite compressive force on inner tubular member 24. Inner tubular member 24 possesses sufficient column strength to prevent buckling or deformation during deployment.

Distal end 32 of inner tubular member 24 has stent holder 34 upon which compressed stent 10 is mounted. Tip assembly 36 having a preferably tapered profile is positioned at distal end 22 of delivery catheter 14 to help cross any areas of occlusions in the diseased artery. Tip assembly 36 is made from a small segment of preferably stainless steel hypotube that has internally tapered wound coil 38 welded to the distal end of tip assembly 36. An optional radiopaque tungsten element 40 is placed at the distal end of tip assembly 36. An opening at the distal end of tip assembly 36 permits guidewire 42 to advance therethrough thereby allowing delivery catheter 14 to track into the diseased artery.

Other aspects of the delivery system are disclosed in co-pending patent application Ser. No. 09/313,780, filed May 17, 1999, entitled "Self-Expanding Stent with Enhanced Delivery Precision and Stent Delivery System," whose entire contents are hereby incorporated by reference. Although this delivery system is used in conjunction with the present invention self-expanding stent, other types of delivery systems are contemplated. For example, the present invention stent may be made of stainless steel or tantalum for example, and may be deployed on a balloon catheter delivery system and balloon expanded at the delivery site. Such balloon delivery systems are well known in the art.

FIG. 3 provides a cross-sectional view of the present invention as deployed in bifurcation 44 between common carotid artery 46 and internal carotid artery 48. It is clear that selection of an appropriate stent diameter becomes important because internal carotid artery 48 tends to be smaller than the parent common carotid artery 46. Furthermore, the denser strut pattern, described below, giving greater hoop strength of stent 10 is important at this particular location to support diseased regions 50.

As seen in FIG. 3, outer tubular member 26 has been withdrawn in the proximal direction exposing stent 10 which self-expands. This is accomplished by fabricating stent 10 from a highly resilient alloy such as superelastic Nitinol or other spring-like materials known in the art.

FIGS. 4 and 5 show expanded and contracted states of stent 10, respectively. As seen in these figures, the preferred embodiment of the present invention stent 10 is constructed from a plurality of nested cylindrical elements 52 arranged coaxially along a common longitudinal stent axis to assume a tubular form. Adjacent cylindrical elements 52 are joined at predetermined circumferential locations by interconnecting members 54 so that each cylindrical element 52 is independently expandable. In the preferred embodiment shown in FIGS. 4 and 5, interconnecting members 54 are aligned axially.

As best seen in FIG. 4, each cylindrical element 52 has a generally serpentine wave strut pattern constructed from repeating patterns of upright and inverted V's 56. Connecting upright and inverted V's 56 are strut arms 58. Each strut arm 58 is generally straight but may include shoulder 60. Optional shoulder 60 is included in strut arm 58 in order to squeeze the stent to a smaller profile in the delivery system. In other words, inclusion of shoulders 60 in strut arms 58 permits tighter packing of the struts of the stent. This leads to better coverage of the vessel wall. Conversely, if strut arms 58 were straight, the vessel coverage by the stent struts is diminished.

Each cylindrical element 52 has a longitudinal dimension or length as measured from peak 84 of one inverted V to valley 86 of the next upright V. Cylindrical elements 52 are described as nested to mean that those lengths of adjacent cylindrical elements 52 overlap each other. Thus, peaks 84 of inverted V's 56 of one cylindrical element 52 lie within the open areas of peaks 84 of inverted V's 56 of adjacent cylindrical elements 52. In a similar fashion, valleys 86 of upright V's 56 of one cylindrical element 52 lie within the open areas of valleys 86 of upright V's of an adjacent cylindrical element 52. This preferred strut arrangement could be described as a loose herringbone pattern.

As best seen in FIG. 4, the lengths of interconnecting members 54 and strut arms 58 increase from first end 64 toward second end 62. Looking at it another way, the strut pattern under this configuration becomes more dense toward first end 64 due to the shorter struts. Taper 82, however, is not created by the varying strut arm lengths 58. Rather, the strut arm lengths 58 is enabled by the taper. The tapering 82 is dictated by the expansion process, that is, the shape of the expansion mandrel when the stent is fabricated. Again, the tapered profile is best seen in the expanded mode of FIG. 4.

Of course, by imparting the length and angle of taper 82 as well as its location on he expansion mandrel, the shape and profiles of the individual strut arms 58 and nterconnecting members 54 are likewise formed. In the embodiment shown in FIG. 4, taper 82 is positioned at a center portion of stent 10. Naturally, taper 82 can be relocated as needed along the length of stent 10.

Taper 82 may be continuous or discrete, and include changes in shape or dimension, with small flares, or tapers only at the ends of the stent. For instance, some types of tapers contemplated in the present invention tapered stent 10 include a step taper as seen in the expanded state of stent 10 in FIG. 4. That is, stent 10 has first end 64 with cylindrical elements 52 at that end having a small constant diameter; second end 62 with cylindrical elements 52 at that end having a large constant diameter; and center section 82 with sequentially changing diameters in cylindrical elements 52 along the longitudinal stent axis to achieve the step taper. Of course, the length and location of center section 82 containing the taper can be changed as necessary to accommodate the specific anatomy of the patient.

The present invention in an alternative embodiment (not shown) further contemplates straight conical tapers; that is, the stent has an angled profile from one end to the opposite end. The shape of the taper in the step diameter change can be varied from straight to parabolic to other shapes as well.

Many physical parameters of the present invention stent can be changed to achieve specific engineering objectives. For example, the density of the strut pattern can be adjusted as needed by varying the lengths of strut arms 58 and interconnecting members 54 to affect the amount of open areas. The included angles of the peaks and valleys of inverted and upright V's 56 can be changed to affect strut density. Increasing the number of inverted and upright V's 56 in a given cylindrical element 52 can also increase strut density. Furthermore, the degree of nesting can be adjusted by only changing the lengths of interconnecting members 54. Shortening interconnecting members 54, for example, would result in a more tightly packed or nested strut pattern. Changing the phase of inverted and upright V's 56 in one cylindrical element 52 to the next can also affect the amount of open space in stent 10, its flexibility, vessel coverage, etc.

Adding or decreasing the number of interconnecting members 54 joining adjacent cylindrical elements 52, positioning them at specific locations around the circumference, and aligning them in a row such as that shown in FIGS. 4 and 5 are all different methods of affecting the stent's hoop strength, foreshortening, flexibility, recoil, and other engineering characteristics. The length of stent 10 can be varied by increasing or decreasing strut arm lengths 58 and interconnecting member lengths 54, by using more or fewer cylindrical elements 52, and by changing the included angles of the inverted and upright V's 56.

In general, the present invention stent is preferably fabricated through manufacturing processes known in the art appropriate for pseudoelastic Nitinol. Other stent materials known in the art, such as stainless steel, are contemplated but not explicitly described here.

First, in the preferred process, the stent strut pattern is laser cut out of a tube stock of pseudoelastic Nitinol. Second, any scale on the surface of the material is removed by bead blast or acid wash.

Third, because the stent is made from Nitinol, it is expanded on an expansion mandrel and heat set. The heat set imparts the shape memory to the alloy, and preferably occurs at approximately 500 to 550 degrees Celsius. After heat set, the stent is quenched in water. Both the heat set and quenching help control the transformation temperature between martensite and austenite of the Nitinol material. Furthermore, the expansion and heat set cycle is performed in stages, sometimes up to five steps, to avoid damaging the stent. The last one or two steps are performed on tapered mandrels to impart the tapered profile. The stent has inherent resilience, which conforms the stent profile to the profile of the tapered mandrels at each stage.

Fourth, the Nitinol stent is electropolished. Preferably, the electropolish solution is a methanol based, acidic mixture. Specifically, the mixture consists of 465 ml absolution methanol, 37.5 mil sulfuric acid (>96.5 percent), and 12.5 ml hydrocloric acid (saturated), which combined produces approximately 500 ml of solution.

The stent is placed in an electropolish fixture preferably constructed from four round, Nitinol wires acting as anodes to hold the stent. The four anode wires are placed around the circumference of the stent, parallel to the stent's longitudinal axis. There is a center cathode made of a platinum rod. The cathode is located at the center of the four anode wires and extends through the center of the stent, parallel and coextensive with its longitudinal axis. The negatively charged center cathode is used to complete the circuit in the solution to polish the inside diameter of the stent.

A curved sheath cathode made of platinum mesh is located parallel to the longitudinal stent axis and partially surrounding the Nitinol wires. The curved sheath cathode is used to complete the circuit in the solution to polish the outside diameter of the stent. The curved sheath is placed just below the four holding anodes, wherein the distance between the sheath and the stent is determined by the size of the part needed to be polished. The fixture and stent positioned thereon are immersed in the solution described above and an electrical current is applied to the circuit.

Fifth, after electropolish, the stent diameter is reduced for fitment with a delivery system. Sixth, the stent is loaded in a delivery system. The end result is a stent with varying diameter along its length as illustrated in FIGS. 4 and 5.

A tapered stent such as in the present invention presents a logical solution for carotid stenting across the bifurcation. The varying stent diameter allows adequate treatment of a lesion in both the common and internal carotid arteries, while maintaining a suitable stent-to-artery ratio for each vessel.

A tapered stent can be applied to other parts of the vascular system where a bifurcation is present such as the coronary arteries and relevant areas where peripheral vascular disease may exist. Tapered stent diameters, lengths, flexibility, radiopacity, and radial hoop strength are all features that would be optimized depending on the expected application of the present invention stent.

FIG. 6 provides a flattened, plan view strut pattern of an alternative embodiment stent 66. Stent 66 is preferably constructed from a plurality of cylindrical elements 68 arranged along a common, longitudinal stent axis to assume a tubular form. Each cylindrical element has decreasing lengths from first end 70 to second end 72 of stent 66, similar to the embodiment depicted in FIGS. 4 and 5.

In FIG. 6, each cylindrical element 68 is formed from struts arranged in a repeating serpentine wave patterns. Interconnecting members 74 join adjacent cylindrical elements 68. In this exemplary embodiment, the serpentine wave pattern is made from alternating U's and W's joined by straight strut arms 80. Each interconnecting member 74 joins W's 78 to U's 77.

Formation of the taper at any portion along the length of stent 66 can be achieved through processing steps described above. FIG. 6 does not show the taper because stent 66 is in the unexpanded state.

The shorter cylindrical elements 68 near second end 72 improve the radial strength and also increase vessel coverage. Opposite second end 72 has longer straight strut arms 80 to allow expansion to larger diameters although the radial force and vessel coverage are reduced.

Clearly, there are other parameters that could also be varied to optimize performance at each end. For example, the stent struts could be varied in width or thickness. The material processing conditions could be varied to impart different engineering characteristics. The number of repeating patterns that form the serpentine wave pattern around the circumference of cylindrical element 68 could be changed. The number of cylindrical elements 68 and the number of interconnecting elements 74 may be varied to change flexibility and other typical design parameters.

While the present invention has been illustrated and described in terms of its use as carotid stents, it will be apparent to those skilled in the art that the present invention stent can be used in other instances in all lumens in the body. Since the present invention stent has the novel feature of self-expansion to a large diameter while retaining its structural integrity, it is particularly well suited for implantation in almost any vessel where such devices are used. This feature, coupled with limited longitudinal foreshortening of the stent when it is radially expanded, provide a highly desirable support member for all vessels in the body. Other modifications and improvements may be made without departing from the scope of the present invention.

What is claimed is:

1. A longitudinally flexible stent for implanting in a body lumen and expandable from a contracted state to an expanded state, comprising:

a plurality of adjacent cylindrical elements, each cylindrical element having a circumference extending around a longitudinal stent axis and being substantially independently expandable in the radial direction, wherein each cylindrical element is formed from struts arranged in a serpentine pattern;

wherein the serpentine pattern is a repeating strut pattern of upright V's and inverted V's which are in phase with the strut pattern of upright V's and inverted V's of an adjacent cylindrical element; and wherein the strut pattern of upright V's and inverted V's of one cylindrical element nest into the upright V's and inverted V's of the adjacent cylindrical element;

wherein the plurality of adjacent cylindrical elements are arranged in alignment along the longitudinal stent axis, and wherein a plurality of cylindrical elements include sequentially increasing diameters to create a tapered profile;

a plurality of interconnecting members extending between the adjacent cylindrical elements and connecting the adjacent cylindrical elements to one another; and wherein the plurality of struts and interconnecting members at the tapered profile increase in length along the longitudinal stent axis.

2. A longitudinally flexible stent for implanting in a body lumen and expandable from a contracted state to an expanded state, comprising:

a plurality of adjacent cylindrical elements, each cylindrical element having a circumference extending around a longitudinal stent axis and being substantially independently expandable in the radial direction, wherein the plurality adjacent cylindrical elements are arranged in alignment along the longitudinal stent axis and define a first end, a second end, and a center section;

wherein the center section is tapered when expanded such that the first end includes a small diameter and the second end includes a large diameter;

each cylindrical element formed from struts arranged in a serpentine wave pattern comprising a repeating strut pattern of upright V's and inverted V's with each upright V and inverted V including a shoulder;

a plurality of interconnecting members extending between the adjacent cylindrical elements and connecting the adjacent cylindrical elements to one another; and wherein the struts and interconnecting members increase in length along the longitudinal stent axis.

* * * * *

UNITED STATES PATENT AND TRADEMARK OFFICE
CERTIFICATE OF CORRECTION

PATENT NO. : 6,569,193 B1
DATED : May 27, 2003
INVENTOR(S) : Daniel L. Cox et al.

It is certified that error appears in the above-identified patent and that said Letters Patent is hereby corrected as shown below:

Title page,
Item [56], U.S. PATENT DOCUMENTS, add:

```
-- 5,421,995   6/1995    Lau et al.
   5,716,393   2/1998    Lindenberg et al.
   5,755,769   5/1998    Richard et al.
   6,010,530   1/2000    Goicoechea
   6,159,208   12/2000   Billion et al.
   6,171,334   1/2001    Cox --.
```

FOREIGN PATENT DOCUMENTS, add:

```
-- WO    WO 32544 A1   9/1997
   WO    WO 99/17680   4/1999
   WO    WO 99/39661   8/1999
   WO    WO 00/28922   5/2000 --.
```

Column 8,
Line 64, before the period, add -- such that the strut pattern is more dense at one end of the longitudinal stent axis than at the other --.

Column 10,
Line 9, before the period, add -- such that the strut pattern is more dense at one end of the longitudinal stent axis than at the other --.

Signed and Sealed this

Nineteenth Day of August, 2003

JAMES E. ROGAN
*Director of the United States Patent and Trademark Office*